(12) United States Patent
Metz et al.

(10) Patent No.: US 6,704,954 B2
(45) Date of Patent: *Mar. 16, 2004

(54) GAP FILLER FOR BED

(75) Inventors: Darrell L. Metz, Batesville, IN (US); John P. Biondo, Aurora, IN (US); Tanya Taber, Lawrenceburg, IN (US); Gregory W. Branson, Batesville, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/190,144

(22) Filed: Jul. 3, 2002

(65) Prior Publication Data

US 2002/0170113 A1 Nov. 21, 2002

Related U.S. Application Data

(62) Division of application No. 09/528,372, filed on Mar. 17, 2000, now Pat. No. 6,427,264.
(60) Provisional application No. 60/125,375, filed on Mar. 19, 1999.

(51) Int. Cl.[7] ............................ A47C 21/08; A61G 7/00
(52) U.S. Cl. ................................. 5/425; 5/600; 5/651
(58) Field of Search ........................... 5/425, 600, 427, 5/426, 428, 429, 424, 513, 516, 651

(56) References Cited

U.S. PATENT DOCUMENTS

| 421,656 A | 2/1890 | Blanken |
|---|---|---|
| 993,119 A | 5/1911 | Standard |
| 1,398,203 A | 11/1921 | Schmidt |
| 2,136,088 A | 11/1938 | Stevens, Sr. |
| 2,164,484 A | 7/1939 | Wolfe |
| 2,281,209 A | 4/1942 | Smith |
| 2,452,366 A | 10/1948 | Freund |
| 2,556,591 A | 6/1951 | Loxley |
| 2,564,083 A | 8/1951 | Stechert |
| 2,605,151 A | 7/1952 | Shampaine |
| 2,644,173 A | 7/1953 | James |
| 2,710,976 A | 6/1955 | Martensen |
| 2,766,463 A | 10/1956 | Bendersky |
| 2,869,614 A | 1/1959 | Wamsley |
| 2,951,252 A | 9/1960 | Roche |
| 3,010,121 A | 11/1961 | Breach |
| 3,018,492 A | 1/1962 | Rosen |
| 3,053,568 A | 9/1962 | Miller |
| 3,099,440 A | 7/1963 | Burzlaff |
| 3,112,500 A | 12/1963 | MacDonald |
| 3,138,805 A | 6/1964 | Piazza |
| 3,148,387 A | 9/1964 | Sarnie et al. |
| 3,210,779 A | 10/1965 | Herbold |
| 3,220,021 A | 11/1965 | Nelson |
| 3,220,022 A | 11/1965 | Nelson |
| 3,233,255 A | 2/1966 | Propst |
| 3,239,853 A | 3/1966 | MacDonald |
| 3,309,717 A | 3/1967 | Black |
| 3,321,779 A | 5/1967 | Kaufman et al. |
| 3,406,772 A | 10/1968 | Ahrent et al. |
| 3,456,269 A | 7/1969 | Goodman |

(List continued on next page.)

FOREIGN PATENT DOCUMENTS

| FR | 1450817 | 8/1966 |
|---|---|---|
| GB | 1466080 | 3/1977 |
| GB | 2 313 303 A | 11/1997 |
| WO | WO 99/15126 | 4/1999 |

*Primary Examiner*—Alexander Grosz
(74) *Attorney, Agent, or Firm*—Bose McKinney & Evans LLP

(57) ABSTRACT

In accordance with the present disclosure, a gap filler is provided for a bed that includes first and second barriers. The gap filler is configured to substantially fill a gap defined between the first and second barriers.

23 Claims, 11 Drawing Sheets

U.S. PATENT DOCUMENTS

| | | |
|---|---|---|
| 3,619,824 A | 11/1971 | Doyle |
| 3,640,566 A | 2/1972 | Hodge |
| 3,742,530 A | 7/1973 | Clark |
| 3,877,090 A | 4/1975 | Schutz |
| 3,893,197 A | 7/1975 | Ricke |
| 3,897,973 A | 8/1975 | Long et al. |
| 3,916,461 A | 11/1975 | Kerstholt |
| 4,127,906 A | 12/1978 | Zur |
| 4,139,917 A | 2/1979 | Fenwick |
| 4,168,099 A | 9/1979 | Jacobs et al. |
| 4,183,015 A | 1/1980 | Drew et al. |
| 4,214,326 A | 7/1980 | Spann |
| 4,215,446 A | 8/1980 | Mahoney |
| 4,232,415 A | 11/1980 | Webber |
| 4,240,169 A | 12/1980 | Roos |
| 4,258,445 A | 3/1981 | Zur |
| 4,312,500 A | 1/1982 | Janssen |
| 4,336,621 A | 6/1982 | Schwartz et al. |
| 4,370,765 A | 2/1983 | Webber |
| 4,409,695 A | 10/1983 | Johnston et al. |
| 4,439,880 A | 4/1984 | Kocelik et al. |
| 4,453,732 A | 6/1984 | Assanah et al. |
| D276,112 S | 10/1984 | Ferrell et al. |
| 4,557,471 A | 12/1985 | Pazzini |
| 4,607,402 A | 8/1986 | Pollard |
| 4,654,903 A | 4/1987 | Chubb et al. |
| 4,670,923 A | 6/1987 | Gabriel et al. |
| 4,672,698 A | 6/1987 | Sands |
| 4,675,926 A | 6/1987 | Lindblom et al. |
| 4,676,687 A | 6/1987 | Koffler |
| 4,685,159 A | 8/1987 | Oetiker |
| 4,704,750 A | 11/1987 | Wheelock |
| 4,710,049 A | 12/1987 | Chang |
| 4,710,992 A | 12/1987 | Falwell et al. |
| 4,745,647 A | 5/1988 | Goodwin |
| 4,751,754 A | 6/1988 | Bailey et al. |
| 4,767,419 A | 8/1988 | Fattore |
| 4,768,249 A | 9/1988 | Goodwin |
| 4,783,864 A | 11/1988 | Turner |
| 4,800,600 A | 1/1989 | Baum |
| 4,827,545 A | 5/1989 | Arp |
| 4,847,929 A | 7/1989 | Pupovic |
| 4,858,260 A | 8/1989 | Failor et al. |
| 4,862,529 A | 9/1989 | Peck |
| 4,862,530 A | 9/1989 | Chen |
| 4,872,228 A | 10/1989 | Bishop |
| 4,873,734 A | 10/1989 | Pollard |
| 4,894,876 A | 1/1990 | Fenwick |
| 4,944,055 A | 7/1990 | Shainfeld |
| 4,974,905 A | 12/1990 | Davis |
| 5,010,611 A | 4/1991 | Mallett |
| 5,035,014 A | 7/1991 | Blanchard |
| 5,040,253 A | 8/1991 | Cheng |
| 5,044,025 A | 9/1991 | Hunsinger et al. |
| 5,072,463 A | 12/1991 | Willis |
| 5,077,843 A | 1/1992 | Foster et al. |
| 5,083,332 A | 1/1992 | Foster et al. |
| 5,084,925 A | 2/1992 | Cook |
| 5,097,550 A | 3/1992 | Marra, Jr. |
| 5,175,897 A | 1/1993 | Marra, Jr. |
| 5,179,744 A | 1/1993 | Foster et al. |
| 5,191,663 A | 3/1993 | Holder et al. |
| 5,193,633 A | 3/1993 | Ezenwa |
| 5,205,004 A | 4/1993 | Hayes et al. |
| 5,230,113 A | 7/1993 | Foster et al. |
| 5,279,010 A | 1/1994 | Ferrand et al. |
| 5,381,571 A | 1/1995 | Gabhart |
| 5,410,765 A | 5/1995 | Youngblood |
| 5,421,046 A | 6/1995 | Vande Streek |
| 5,450,641 A | 9/1995 | Montgomery |
| 5,454,126 A | 10/1995 | Foster et al. |
| 5,455,973 A | 10/1995 | Brumfield et al. |
| 5,479,666 A | 1/1996 | Foster et al. |
| 5,481,772 A | 1/1996 | Glynn et al. |
| 5,485,699 A | 1/1996 | Gabhart |
| 5,524,306 A | 6/1996 | George |
| 5,557,817 A | 9/1996 | Haddock |
| 5,577,277 A | 11/1996 | Sundberg et al. |
| 5,577,279 A | 11/1996 | Foster et al. |
| 5,642,545 A | 7/1997 | Howard |
| 5,671,490 A | 9/1997 | Wu |
| 5,689,839 A | 11/1997 | Langaniere et al. |
| 5,715,548 A | 2/1998 | Weismiller et al. |
| 5,732,423 A | 3/1998 | Weismiller et al. |
| 5,745,937 A | 5/1998 | Weismiller et al. |
| 5,749,112 A | 5/1998 | Metzler |
| 5,761,756 A | 6/1998 | Nowak et al. |
| 5,771,506 A | 6/1998 | Joiner et al. |
| 5,781,945 A | 7/1998 | Scherer et al. |
| 5,802,636 A | 9/1998 | Corbin et al. |
| 5,864,900 A | 2/1999 | Landau |
| 5,926,873 A | 7/1999 | Fountain |
| 6,089,593 A | 7/2000 | Hanson et al. |

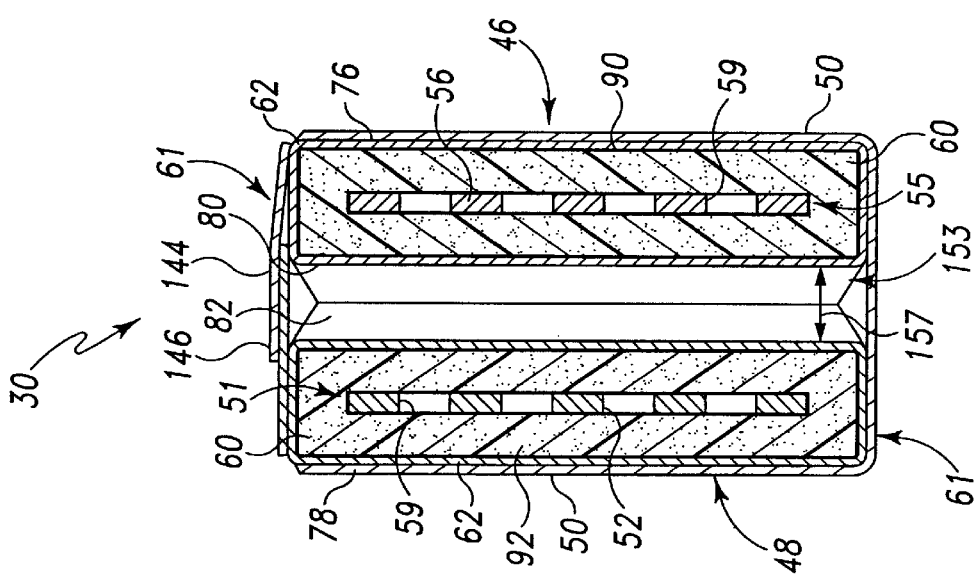
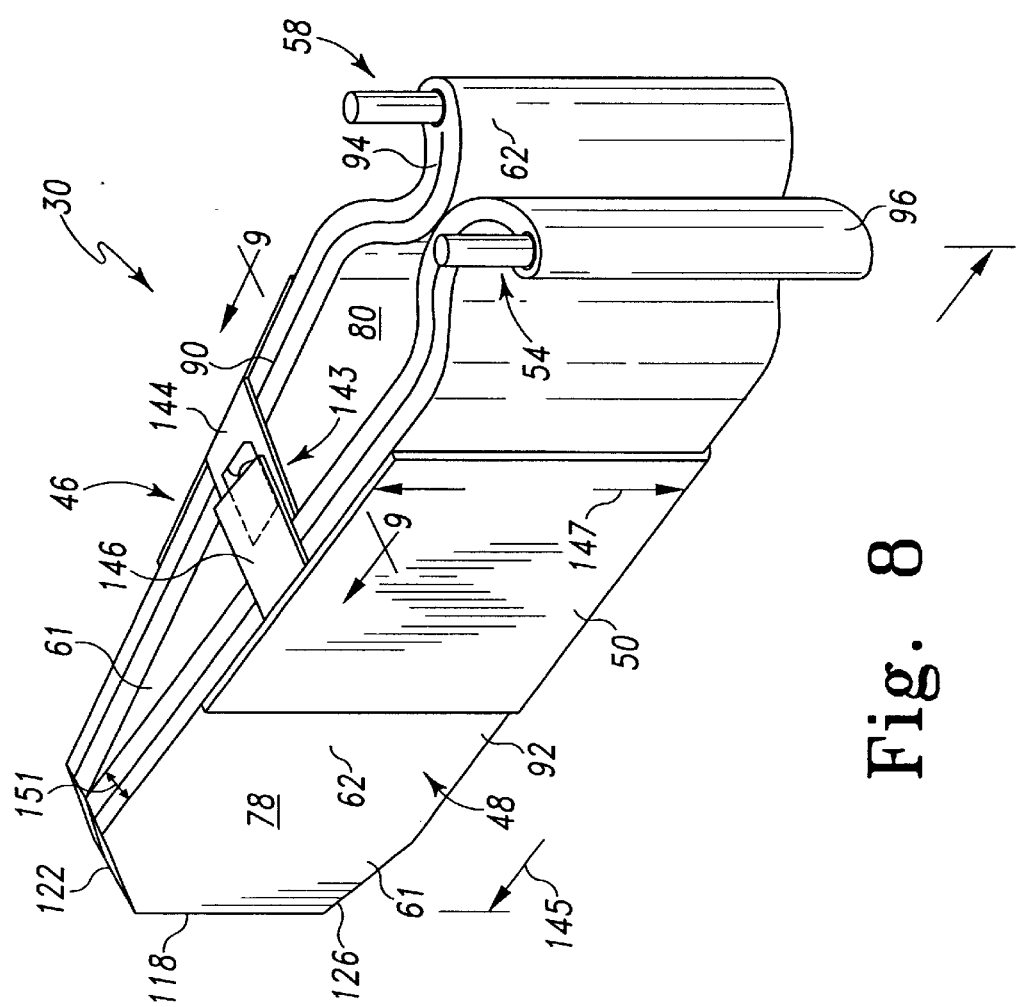
Fig. 9
Fig. 8

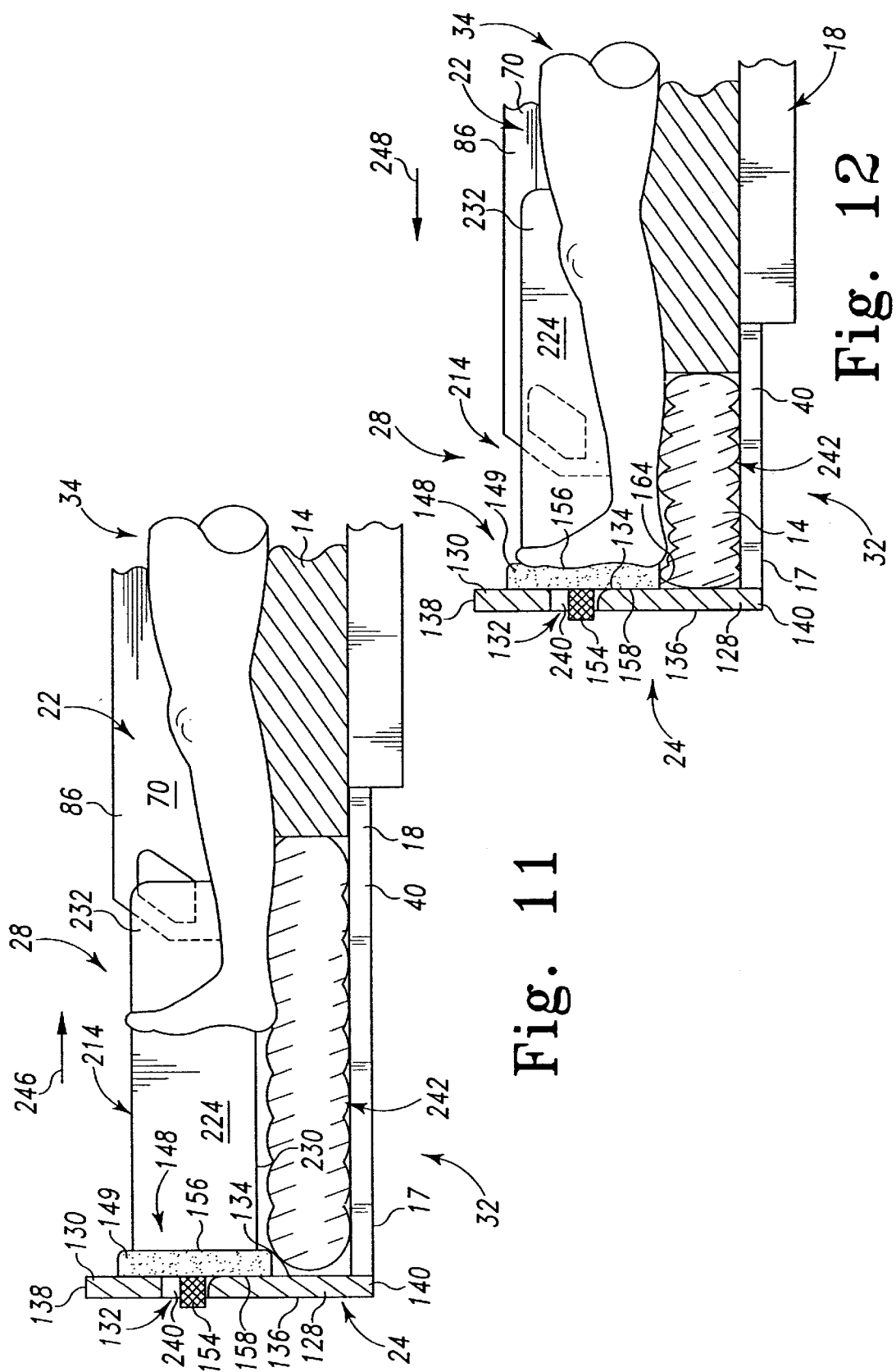

GAP FILLER FOR BED

This application is a divisional of U.S. application Ser. No. 09/528,372, filed Mar. 17, 2000, now U.S. Pat. No. 6,427,264B1 which claims the benefit of U.S. Provisional Application Ser. No. 60/125,375 filed Mar. 19, 1999, the disclosures of which are expressly incorporated by reference herein.

BACKGROUND AND SUMMARY OF THE INVENTION

The present invention relates to accessories for hospital beds and particularly to a hospital bed having barriers such as siderails, footboards, and headboards defining gaps therebetween. More particularly, the present invention relates to devices configured to close or fill the gaps defined between the barriers.

It is known to provide beds with foot supporting sections which are extendable and retractable and which may be articulated downwardly, in conjunction with articulation of the head section upwardly, to form a chair-type structure. One example of a hospital bed which provides both of these functions is described in U.S. Pat. No. 5,715,548, which is expressly incorporated herein by reference. A commercial embodiment of a bed incorporating both of these features is sold by HillRom, Inc., Batesville, Ind. under the brand name The TotalCare® Bed System.

When the foot section of the bed is retracted, a footboard coupled to the foot section approaches both the heel of the patient and a foot end siderail. The gap between the foot end siderail and the footboard decreases as the foot section is retracted. The footboard is constructed of rigid materials which is eventually brought into direct contact with the patients' feet.

According to the present invention, a bed is provided including a bedframe having a head end and a foot end, a mattress positioned on the bedframe, a siderail coupled to the bedframe, and a board coupled to one of the head and foot ends of the bedframe. The siderail and the board cooperate to define a gap therebetween. The bed further includes a gap filler coupled to the board to extend between the board and the siderail to substantially fill the gap defined therebetween.

According to another aspect of the present invention, a bed is provided including a bedframe, a mattress positioned on the bedframe, a first barrier coupled to the bedframe, and a second barrier coupled to the bedframe. The first and second barriers cooperate to define a gap therebetween. The bed further includes a gap filler positioned to extend between the first and second barriers to substantially fill the gap defined therebetween. The gap filler includes a top surface and a bottom surface positioned to slide on the mattress during movement of the gap filler relative to the mattress.

According to another aspect of the present invention, a bed is provided including a bedframe, a mattress positioned on the bedframe, a siderail coupled to the bedframe, and a footboard coupled to the bedframe. The mattress and the siderail cooperate to define a mattress gap therebetween. The siderail and the footboard cooperate to define a substantial foot end gap therebetween. The bed further includes a gap filler positioned on the mattress to substantially block the foot end gap and block at least a portion of the mattress gap.

Additional features of the disclosure will become apparent to those skilled in the art upon consideration of the following detailed description when taken in conjunction with the accompanying drawings.

BRIEF DESCRIPTION OF THE DRAWINGS

The detailed description particularly refers to the accompanying figures in which:

FIG. 8 is a perspective view of the gap filler showing the gap filler removed from the frame and the tabs having the hook-and-loop type fasteners coupled together to hold the barriers adjacent one another;

FIG. 9 is a sectional view taken along line 9—9 of FIG. 8;

FIG. 11 is a sectional view taken along line 11—11 of FIG. 10 showing the foot section in the extended position;

FIG. 12 is view similar to FIG. 11 showing the foot section in the retracted position with a patient's foot contacting the footpad;

DETAILED DESCRIPTION OF THE DRAWINGS

Figure 1:
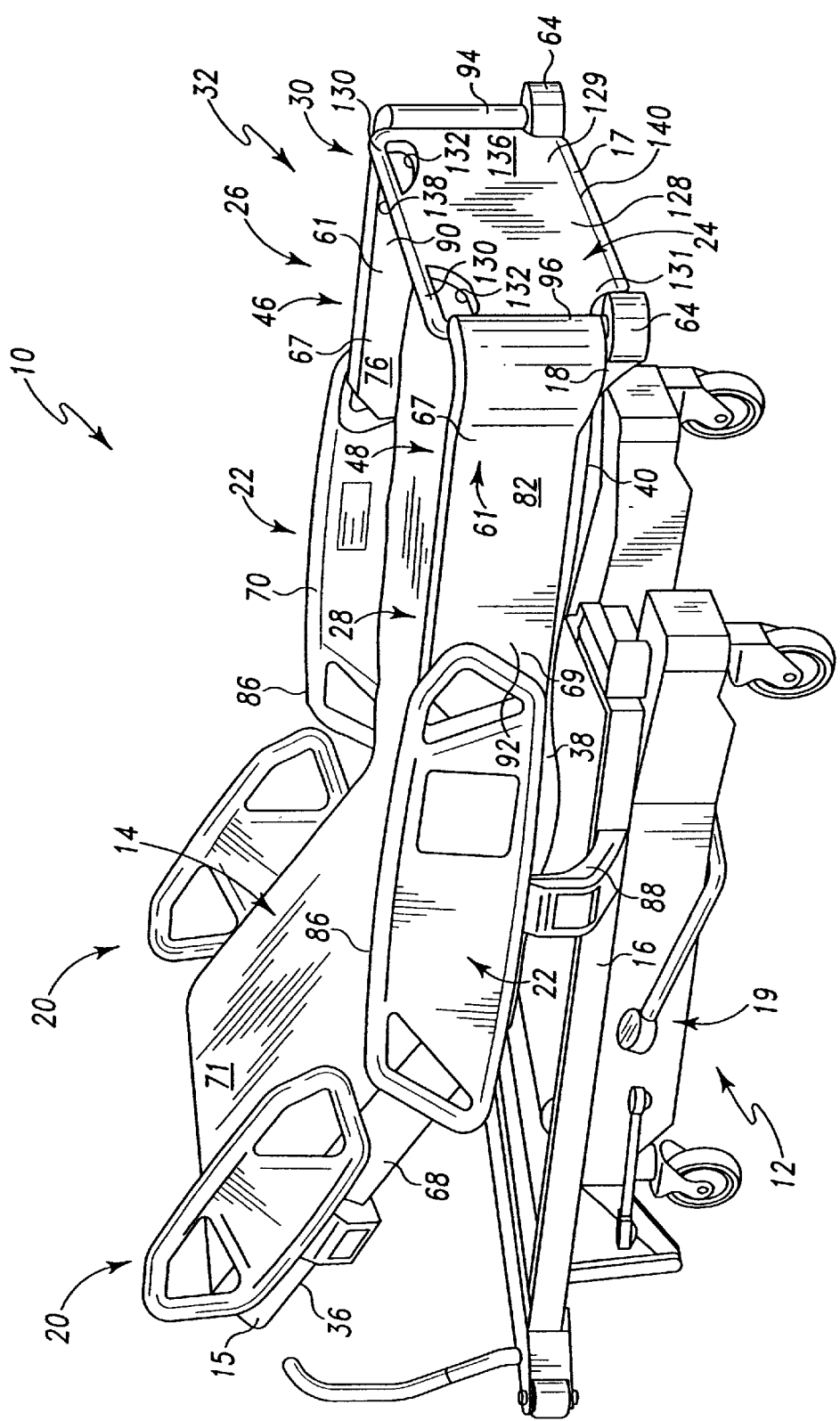
FIG. 1 is a perspective view of a hospital bed showing the hospital bed including a bedframe and a mattress positioned on the bedframe, the bedframe including an intermediate frame and an articulating deck, the bed further including a pair of head end siderails coupled to the bedframe, a pair of foot end siderails coupled to the bedframe, and a gap filler extending between the footboard and the foot end siderail.
Figure 5:
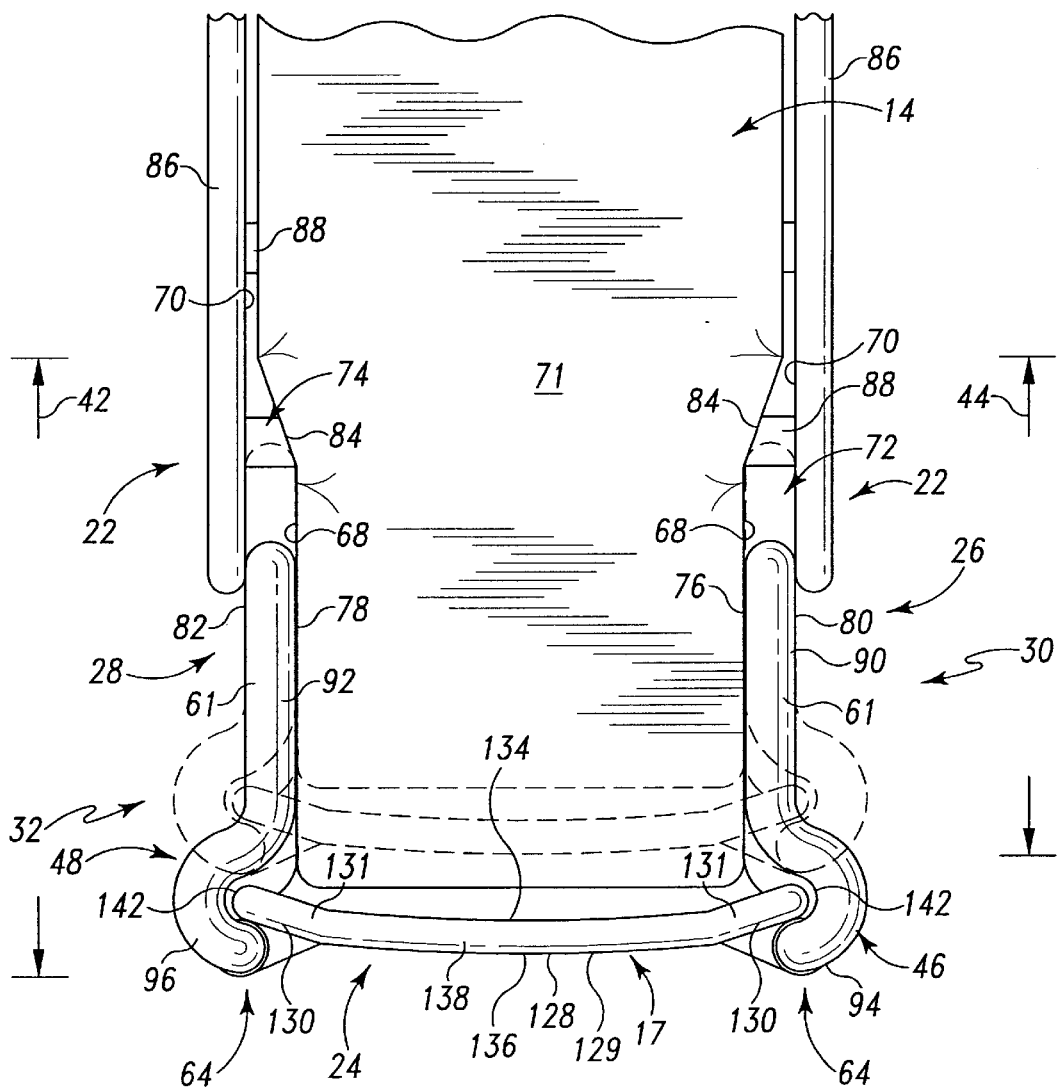
FIG. 5 is a top plan view of the foot end of the hospital bed showing the retractable foot section in the extended position, the foot section in the retracted position (in phantom), and the barriers of the gap filler sliding in a space defined between the siderail and mattress.

As shown in FIG. 1, a hospital bed 10 is provided for supporting a patient (not shown). Hospital bed 10 includes a bedframe 12 and a mattress 14 positioned on top of bedframe 12. Bedframe 12 includes a head end 15, a foot end 17, a base frame 19, an intermediate frame 16 coupled to base frame 19, an articulating deck 18 coupled to intermediate frame 16, and several barriers such as two pair of head and foot end siderails 20, 22 coupled to intermediate frame 16, a footboard 24 coupled to deck 18, and a headboard (not shown) coupled to head end 17. As shown in FIG. 5, footboard 24 and foot end siderails 22 cooperate to define a pair of gaps 26, 28 therebetween. According to the present disclosure, hospital bed 10 further includes a gap filler 30, as shown in FIG. 1, that extends between footboard 24 and foot end siderails 22 to substantially fill in gaps 26, 28 and block movement of a patient from a foot end 32 of hospital bed 10.

Figure 6:
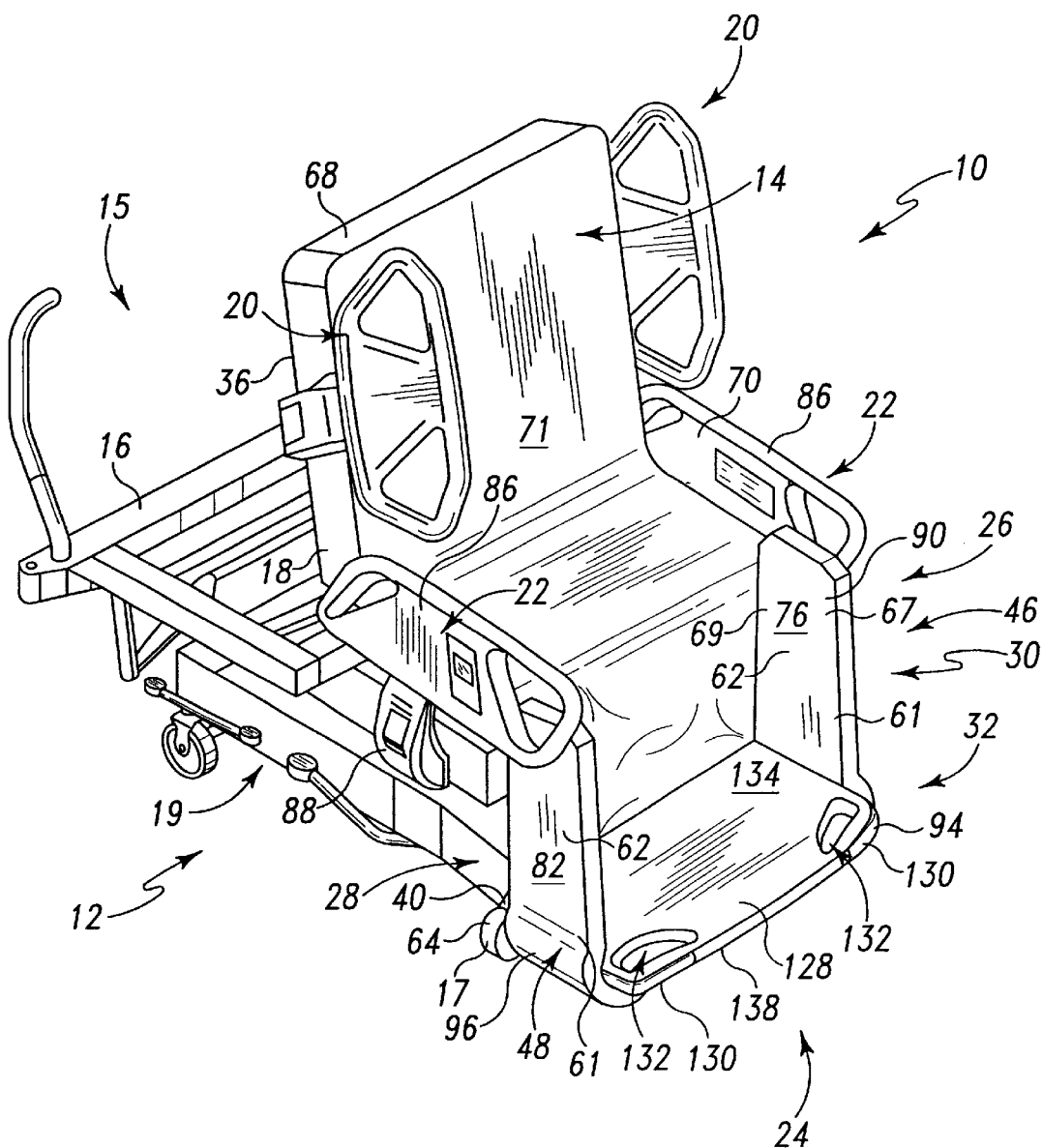
FIG. 6 is a perspective view of the hospital bed of FIG. 1 showing the hospital bed in a chair configuration.
Figure 7:
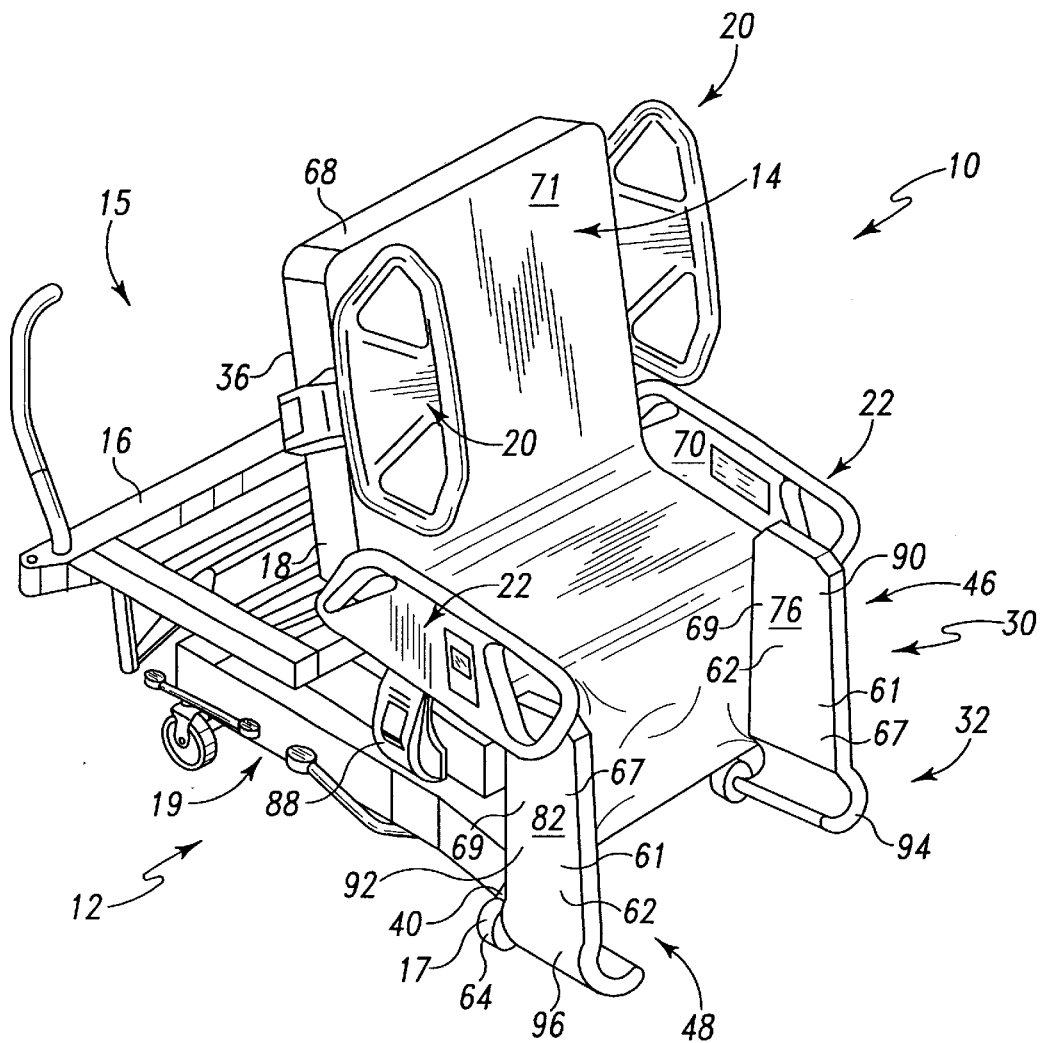
FIG. 7 is a view similar to FIG. 6 showing the footboard removed from the hospital bed.

Siderails 20, 22 are pivotably coupled to intermediate frame 16 so that a caregiver may raise and lower siderails 20, 22 to permit a patient 34 to enter and leave bed 10. Deck 18 includes a head section 36, a seat section 38 pivotably coupled to head section 36, and a foot section 40 pivotably coupled to seat section 38. As shown in FIGS. 6 and 7, deck 18 is configured to move from a bed position, as shown in FIG. 1, to a chair configuration, as shown in FIG. 6, where foot section 40 drops below seat section 38.

Foot section 40 is also retractable. As shown in FIG. 5, foot section 40 moves from an extended position having an extended length 42 to a retracted position having a retracted length 44 that is less than extended length 42. This permits the caregiver to adjust the overall length of bed 10 in either the bed position or the chair position. Additional features and the operation of beds having retractable foot sections are explained in co-pending U.S. Utility patent application Ser. No. 09/120,125, filed Jul. 22, 1998, now U.S. Pat No. 6,212,714 and in Weismiller et al., U.S. Pat. No. 5,715,548, issued Feb. 10, 1998, the disclosures of which are expressly incorporated by reference herein.

Figure 3:
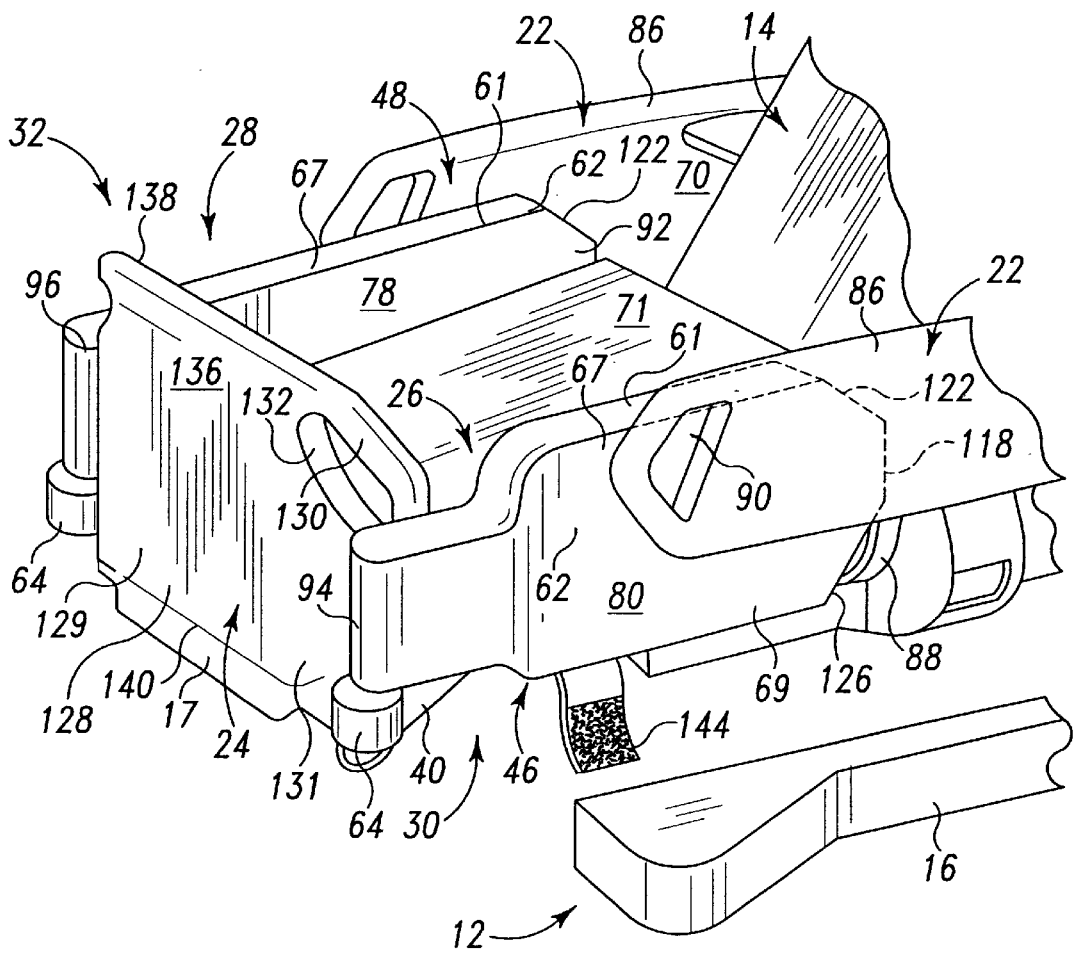
FIG. 3 is a perspective view of a foot end of the hospital bed showing the deck including a retractable foot section in a retracted position with the barriers positioned between the foot end siderails and the mattress.

Patients often do not have full control of their extremities or faculties. As a result, a patient's leg or other body part may move to a position extending off of the surface of mattress 14 through gaps 26, 28. To block this movement, gap filler 30, as shown in FIGS. 1, 3, and 5 is provided for hospital bed 10 to prevent a patient's body part from extending off of the surface of mattress 14. According to alternative embodiments of the present disclosure, the gap filler extends between the head end siderail and the headboard to block the gap defined therebetween.

Figure 2:
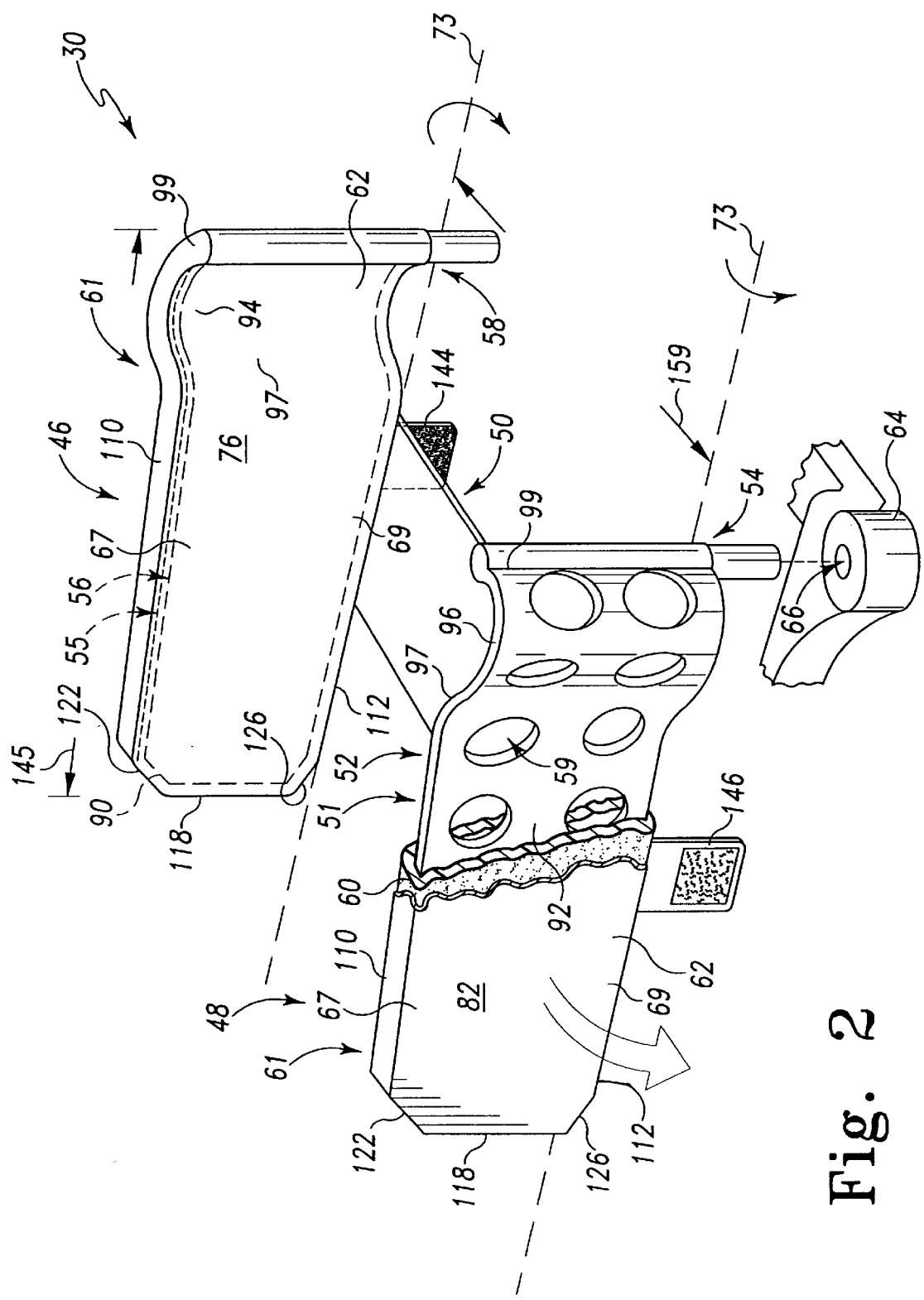
FIG. 2 is a perspective view of the gap filler and a portion of the deck showing the gap filler including a pair of barriers and a web extending between the barriers and each barrier including a frame having a straight and curved panels and a post configured to fit within a socket formed in the deck, a layer of foam positioned over the panels, a cover positioned over the layer of foam, and a pair of tabs having hook-and-loop type fasteners coupled to the cover.

Gap filler 30 includes a right barrier 46, a left barrier 48, and a web 50 extending between right and left barriers 46, 48 as shown in FIG. 2. Right barrier 46 extends from footboard 24 to right siderail 22 to fill gap 26 as shown in FIG. 1. Similarly, left barrier 48 extends from footboard 24 to left siderail 22 to fill gap 28.

As shown in FIG. 2, left barrier 48 includes a frame 51 having a plate-like spine 52 and a post 54 coupled to spine 52. Similarly, right barrier 46 includes a frame 55 having a plate-like spine 56 and a post 58 coupled to spine 56. Spines 52, 56 and posts 54, 58 are preferably made of aluminum. According to alternative embodiments, other rigid or semi-rigid materials are used for the spines and posts such as other metals or plastics materials. As shown in FIG. 2, each spine 52, 56 includes a series of apertures 59 to reduce the overall weight of barriers 46, 48. Each barrier 46, 48 further includes a cover 61 having a layer of resilient material 60, such as foam, positioned over the respective spines 52, 56 for padding and a sheath 62 covering the respective layer of resilient material 60.

As shown in FIGS. 2 and 3, bedframe 12 includes a pair of nodes 64 coupled to foot section 40 of deck 18. Each node 64 includes a socket 66 sized to receive an IV pole (not shown). Posts 54, 58 are sized to fit in sockets 66 to couple right and left barriers 46, 48 to foot section 40 of deck 18.

When posts 54, 58 are positioned in sockets 66, respective spines 52, 56 are cantilevered from posts 54, 56 to extend between foot board 24 and siderails 22 as shown, for example, in FIG. 3.

Figure 4:
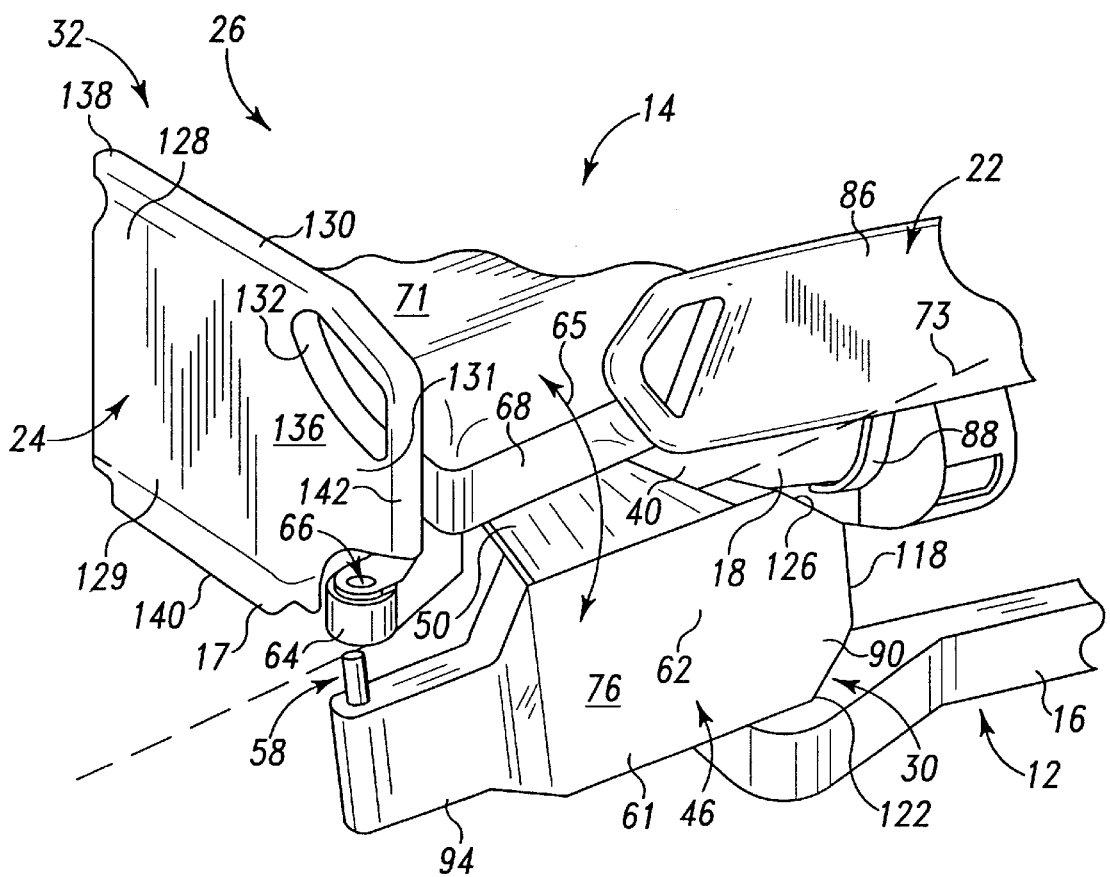
FIG. 4 is a view similar to FIG. 3 showing the retractable foot section in an extended position and one of the barriers removed from the respective pocket of the deck so that the barriers is supported by the web to hang below the mattress.

A caregiver may temporarily move barriers 46, 48 from blocking gaps 26, 28 to permit a patient to exit hospital bed 10. When gap filler 30 is positioned on hospital bed 10, web 50 is positioned on deck 18 so that mattress 14 is positioned on top of web 50. If posts 54, 58 are removed from the respective sockets 66, each respective barrier 46, 48 will hang below the upper support surface of mattress 14 as shown in FIG. 4. Thus, each barrier 46, 48 is hingedly coupled to deck 18 of bedframe 12 by web 50 to pivot in direction 65 about a horizontal axis 73. This permits the caregiver to move respective barriers 46, 48 from a blocking position filling gaps 26, 28, as shown in FIG. 3, to an unblocking position, as shown in FIG. 4, permitting a patient to exit hospital bed 10.

When barriers 46, 48 are coupled to bedframe 12 and web 50 is positioned under mattress 14, web 50 prevents a patient from pushing barriers 46, 48 outwardly opening gaps 26, 28. Web 50 is substantially taut when positioned under mattress 14 as shown, for example, in FIG. 2. Because web 50 is taut, any outward movement of one of barriers 46, 48 urges the other respective barrier 46, 48 inwardly. However, mattress 14 blocks any substantial inward movement of the other respective barrier 48, 46 and because web 50 is taut, web 50 prevents any substantial outward movement of the respective barrier 46, 48. Thus, when gap filler 30 is positioned on bed 10, a patient cannot swing barriers 46, 48 outwardly to open gaps 26, 28 to exit.

When foot end siderails 22 are in an up position, as shown in FIG. 1, they also prevent a patient from swinging barriers 46, 48 outwardly. As shown in FIGS. 1, 3, and 5, each barrier 46, 48 includes an upper portion 67 and a lower portion 69 positioned between the respective foot end siderail 22 and mattress 14. As shown in FIG. 5, mattress 14 includes an upper support surface 71 and a pair of outer surfaces 68. Foot end siderails 22 each include an inner surface 70. Mattress 15 is stepped so that outer surfaces 68 and respective inner surfaces 70 cooperate to define right and left spaces 72, 74 in which lower portions 69 of respective right and left barriers 46, 48 are positioned during normal use as shown in FIG. 5.

Right and left barriers 46, 48 include innermost surfaces 76, 78 and outermost surfaces 80, 82. If a patient attempts to swing either barrier 46, 48 outwardly when respective foot end siderails 22 are in the up position, outermost surfaces 80, 82 will strike inner surface 70 of the respective foot end siderail 22. Thus, when foot end siderails 22 are in the up position, they block any outward movement of barriers 46, 48.

Mattress 14 blocks inward movement of barriers 46, 48 to prevent a patient from pulling barriers 46, 48 inwardly to open gaps 26, 28. If barriers 46, 48 are pulled inwardly, innermost surfaces 76, 78 of barriers 46, 48 strike outer surfaces 68 of mattress 14. Thus, any substantial inward movement of barriers 46, 48 is blocked so that gaps 26, 28 remain blocked.

Barriers 46, 48 are positioned on hospital bed 10 so that gaps 26, 28 remain blocked when foot section 40 is retracted and extended. As shown in FIG. 5, outer surfaces 68 of mattress 14 taper at angled portions 84 so that right and left spaces 72, 74 are also tapered. As foot section 40 retracts, lower portions 69 of barriers 46, 48 slide in right and left spaces 72, 74 relative foot end siderails 22 and mattress 14 toward respective angled portions 84. Because right and left spaces 72, 74 are provided, less resistance to the movement of barriers 46, 48 occurs and gaps 26, 28 remain blocked. Sliding of barriers 46, 48 relative to mattress 14 and foot end siderails 22, also permits hospital bed 10 to move to a reclined chair position, as shown in FIG. 3, with little resistance from gap filler 30. According to alternative embodiments of the present disclosure, mattresses of other configuration are used with the gap filler including mattresses without spaces between the siderail and mattress.

Barriers 46, 48 are also configured to avoid interference with bedframe components and the patient as foot section 40 is retracted. As shown in FIG. 3, foot end siderails 22 include a rail member 86 and a linkage mechanism 88 coupling rail member 86 to intermediate frame 16. Barriers 46, 48 are chamfered to avoid contact with linkage mechanism 88 as they slide forward in spaces 72, 74.

As shown in FIG. 2, each barrier 46, 48 includes a generally straight panel 90, 92 and a curved panel 94, 96 coupled to respective straight panels 90, 92 and respective posts 54, 58. Straight panels 90, 92 and curved panels 94, 96 are defined by respective spines 54, 56, layers of resilient material 60, and sheaths 62. Each curved panel 94, 96 includes a first and second spaced-apart vertical edges 97, 99. Respective first vertical edges 97 are coupled to straight panels 90, 92 and respective second vertical edges 99 are coupled to posts 54, 56.

As shown in FIG. 2, each straight panel 90, 92 includes a top edge 110, a bottom edge 112 a substantially vertical edge 118, a top chamfered edge 122 extending from respective vertical edges 118 to respective top edges 110, and a bottom chamfered edge 126 extending from respective vertical edges 118 to respective bottom edges 112. Chamfered edges 122, 126 are preferably angled at 45° relative to respective vertical edges 118. According to alternative embodiments, the chamfered edges taper at other angles relative to the vertical edge or are rounded. According to yet another alternative embodiment, the chamfered edges and the vertical edges cooperate to define a rounded edge.

Bottom chamfered edges 126 provide clearance between each barrier 46, 48 and linkage mechanism 88 to permit gap filler 30 to avoid striking foot end siderails 22. As barriers 46, 48 move forward during retraction of foot section 40, bottom chamfered edges 126 move over linkage mechanism 88 to avoid interference between barriers 46, 48 and foot end siderails 22. Thus, by tapering barriers 46, 48, additional travel of barriers 46, 48 relative to foot end siderails 22 is provided without interference.

As previously mentioned, bedframe 12 is configured to move between the bed position, as shown in FIG. 1, and the chair position as shown in FIG. 6. When in the chair position, barriers 46, 48 move to a vertical orientation. When in the vertical position, barriers 46, 48 continue to fill gaps 26, 28 as shown in FIG. 6.

Footboard 24 is removable from foot section 40 as shown in FIG. 7. When footboard 24 is removed, a patient seated in hospital bed 10 may stand up from a seated position. As shown in FIG. 3, footboard 24 includes a base 128 removably coupled to foot section 40 of deck 18 and a pair of handles 130 coupled to base 128.

Base 128 includes a substantially planar middle section 129 and two arcuate end sections 131. Middle section 129 includes patient-facing side 134 facing toward mattress 14, a first vertical surface 136 facing away from patient-facing side 134, a top edge 138, and a bottom edge 140. Arcuate end sections 131 include a pair of vertical edges 142 extending from top edge 138 to bottom edge 140.

Vertical edges 142 of footboard 24 are positioned between and adjacent to the respective curved panels 94, 96 of barriers 46, 48. The curvature provided by curved panels 94, 96 permits posts 54, 58 to fit within sockets 66 and barriers 46, 48 to wrap around edges 142 of footboard 24. This also provides clearance between curved panels 94, 96 and footboard 24. This clearance facilitates a caregiver in removing footboard 24 from foot section 40 of deck 18 with little or no interference with barriers 46, 48 so that a patient's feet may reach the floor when assuming the standing position.

Gap filler 30 is also removable from hospital bed 10. To remove gap filler 30 from hospital bed 10, a caregiver removes posts 54, 58 from sockets 66 as shown in FIG. 2. The caregiver then folds a foot end of mattress 14 toward a head end of hospital bed 10 and web 50 is accessible so that gap filler 30 can be removed from foot section 40 of deck 18.

After removal, a caregiver can fold gap filler 30 into to a compact size for storage as shown in FIG. 8. To fold gap filler 30 to the storage position, the caregiver folds barriers 46, 48 inwardly so that innermost surfaces 76, 78 lie against web 50. Then the caregiver folds barriers 46, 48 inwardly again so that outermost surfaces 80, 82 are adjacent one another as shown in FIGS. 8 and 9. Gap filler 30 further includes a pair of tabs 144, 146 coupled to sheaths 62 of respective barriers 46, 48. Coupled to tabs 144, 146 are Velcro-brand hook-and-loop fasteners that couple to one another to couple barriers 46, 48 together in the storage position. Tabs 144, 146 cooperate to define a handle 143 to facilitate carrying gap filler 30 when removed from bed 10.

When in the storage position, barriers 46, 48 are positioned adjacent to one another and web 50 is positioned around left and right barriers 46, 48. As shown in FIGS. 8 and 9, each barrier has a length 145, a width 147, and a thickness 151. As shown in FIG. 9, right and left barriers 46, 48 cooperate to define a space 153 therebetween having a width 157. Web 50 has a length 159 (shown best in FIG. 2) approximately equal to the sum of widths 147 and thicknesses 151 of barriers 46, 48 and width 157 of space 153 so that web 50 wraps around left and right barriers 46, 48. According to alternative embodiments, the barriers lie substantially flat together when in the storage position so that a space defined therebetween is very small having a width that is also very small.

Figure 13:
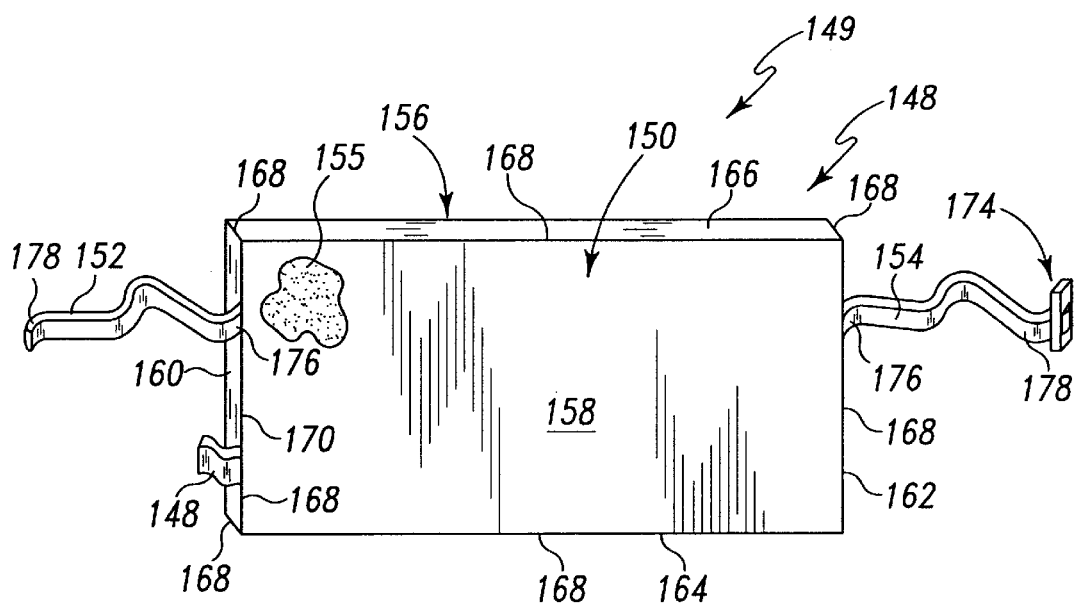
FIG. 13 is a perspective view of the footpad.

When foot supporting section 40 of bed 10 is retracted, it is typically retracted until rigid footboard 24 comes into contact with the patient's outstretched feet. During retraction foot section 242 of the air mattress section is often deflated, as shown, for example, in FIG. 12, to relieve stress on the patient's heel. To minimize any discomfort resulting from contact of footboard 24 with the patient's outstretched feet, a footpad 148 is attached to patient-facing side 134 of footboard 24. Footpad 148 in accordance with the present disclosure includes a cushion 149 and straps 152, 154 for attaching cushion 149 to footboard 24 of bed 10. As shown in FIG. 13, cushion 149 includes a cover 150 having external dimensions sized to be received on footboard 24 and an internal compressible filler 155. The described footpad 148 is specifically configured for use with the commercial version of the TotalCare® Bed System, but it is to be understood that other configurations of footpads adapted for use with other beds having retractable foot supporting sections are within the teaching of the disclosure.

Cover 150 of footpad 148 is formed from a suitable material such as PENN-NYLA material, a water impermeable material. As shown in FIG. 13, cover 150 is a substantially rectangular box shape and includes a foot-engaging surface 156, a footboard-engaging surface 158, a left side wall 160, a right side wall 162, a bottom side wall 164, and a top side wall 166. Each side wall 162, 160, 164, 166 extends between foot-engaging surface 156 and footboard-engaging surface 158 to form cover 150 having an interior. Foot-engaging surface 156 and footboard-engaging surface 158 of cover 150 are both rectangular. Cover 150 may be formed from multiple panels or from an appropriately configured single panel.

In the illustrated embodiment seams 168 are formed between left side wall 160 and top side wall 166, left side wall 160 and footboard-engaging surface 158, top side wall 166 and footboard-engaging surface 158, right side wall 162 and footboard-engaging surface 158, right side wall 162 and top side wall 166, right side wall 162 and bottom side wall 164, bottom side wall 164 and footboard-engaging surface 158, and bottom side wall 164 and left side wall 160. Each of these seams 168, with the exception of seam 170 between left side 160 wall and footboard-engaging surface 158 are formed by ultrasonic welding the material forming the panels. Seam 170 between left side wall 160 and footboard-engaging surface 158 is not initially welded to facilitate insertion of filler 155 and attachment of tags 148. Initially seam 170 is left open providing an opening to the interior of cover 150.

In the illustrated embodiment internal compressible filler 155 is formed from a single block of compressible foam material. A fire barrier, not illustrated is positioned between the foam material block and the cover. During assembly all of seams 168 of cover 150 are ultrasonic welded as described above leaving an opening along the length of seam 170 between left side wall 160 and footboard-engaging surface 158. Internal compressible filler block 110 is compressed and inserted through the opening and manipulated to expand to fill the interior of cover 150. Required tags 148 are then inserted in length of seam 170 between left side wall 160 and footboard-engaging surface 158 and length of seam 170 is sewn shut.

Footpad 148 also includes straps 152, 154 having buckle 174 to facilitate attachment of footpad 148 to footboard. Both straps 152, 154 have a first end 176 and a second end 178. Illustratively both straps 152, 154 are formed of PENN-NYLA material. First end 176 of strap 152 is ultrasonic welded to right side of footboard-engaging surface 158. First end 176 of strap 154 is ultrasonic welded to left side of footboard-engaging surface 158. Buckle 174 is slid past second end 178 of strap 154 to be received on strap 154 which is then folded over upon, and RF welded to, itself to secure buckle 174 to strap 154.

To attach footpad 148 to footboard 24, footboard-engaging surface 158 is placed against patient-facing side 102 of footboard 24. Strap 152 is then inserted through one hand hole 132 and strap 154 is inserted through the other hand hole 132. Second end 178 of strap 152 is inserted through buckle 174 on strap 154 and pulled taut to secure footpad 148 to footboard 138.

An alternative embodiment gap filler 210 is shown in FIGS. 10–12 and 14. Gap filler 210 includes a pair of barriers 212, 214 and straps 216 coupling barriers 212, 214 to footboard 24. Strap 216 includes connectors 222 for securing gap filler 210 to footboard 24. Each barrier 212, 214 includes a cover 218 and a resilient compressible filler 220 positioned within cover 218.

Figure 14:
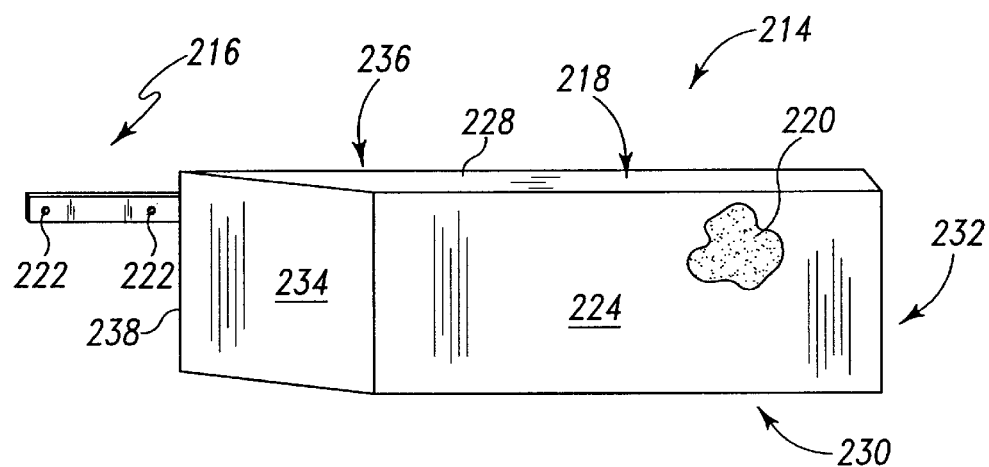
FIG. 14 is a perspective view of one of the barriers of FIG. 10.

Cover 218 is formed to include a patient-facing surface 224 and a spaced apart substantially parallel rail-facing surface 226. As shown in FIG. 14, a top surface 228, a bottom surface 230, and an end surface 232 extend substantially perpendicularly between patient-facing surface 224 and rail-facing surface 226. Cover 218 also includes an inclined wall 234 extending between patient-facing surface 224 and rail-facing surface 226 to form a footboard-engaging wedge 236. Inclined surface 234 joins patient-facing surface 224 at an acute angle, as shown, for example, in FIG. 14, illustratively cover 218 is formed from PENN-NYLA material and may be formed from properly configured single or multi-panels appropriately joined together in the shape shown in FIG. 14.

Illustratively compressible filler 220 is formed from a single block of foam material and is sized to fit within the interior of cover 218. Filler 220 of gap filler 210 is stiffer than foam material used for filler 155 in footpad 148. This additional stiffness is the result of the use of less compressible foam or thicker foam in forming gap filler 210 as compared to footpad 148.

Strap 216 is attached to seam 238 formed between inclined surface 234 and patient-facing surface 224. Strap 216 is sized to wrap around an outer portion 240 of handle 130 formed in blow molded footboard 24 as shown, for example, in FIG. 10. Strap 216 includes connectors 222, such as snaps, so that connectors 222 can be joined after strap 216 is wrapped around handle 130 to secure gap filler 210 to footboard 24.

It should be understood that gap filler 210 described herein is specifically configured for use with the commercial version of the TotalCare® Bed System, but that barriers configured for other beds having retractable or non-retractable foot sections are within the teachings of the disclosure. According to alternative embodiments of the present disclosure, the gap filler extends between the head end siderail and the headboard.

Figure 10:
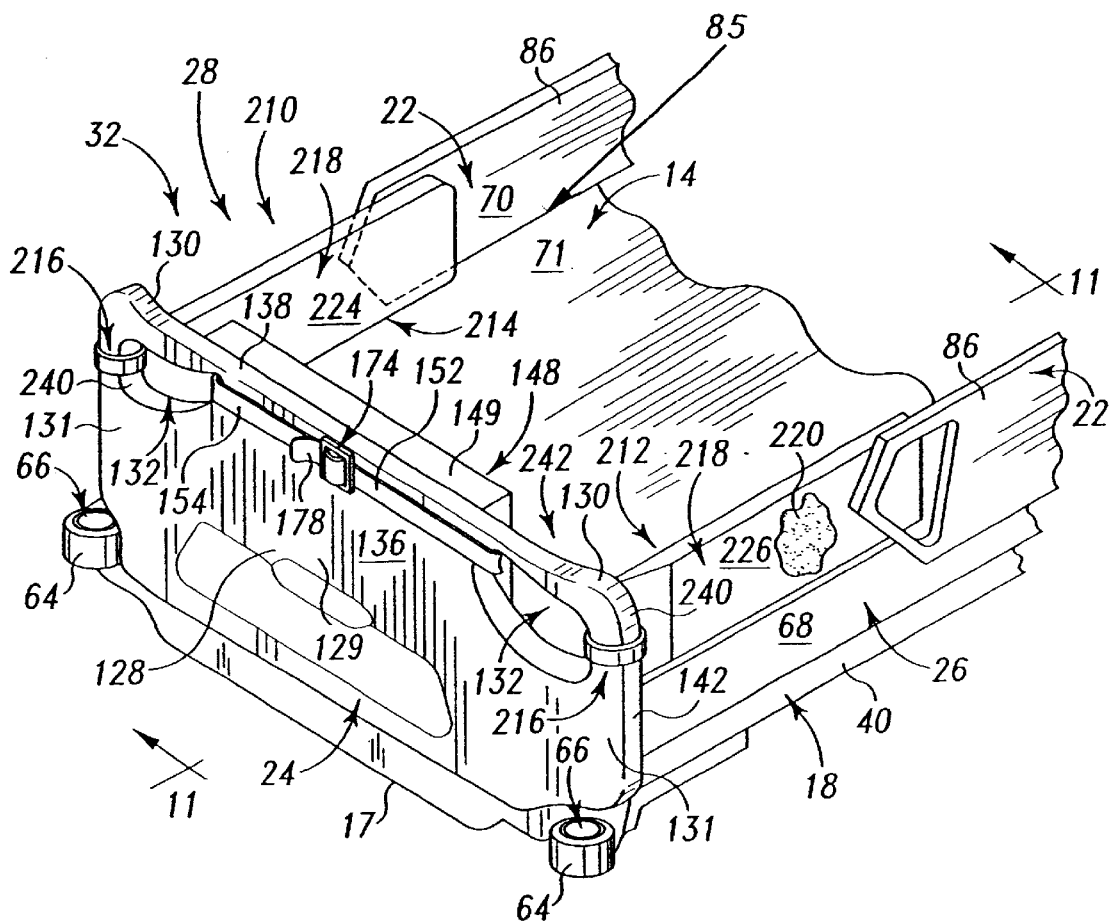
FIG. 10 is a perspective view of an alternative embodiment gap filler including a pair of barriers coupled to handles of the footboard by straps with the barriers extending between the footboard and foot end siderails to close the gap therebetween and a footpad coupled to the footboard by a strap extending between hand holes in the footboard of the bed.

When attached to bed 10, bottom surface 230 of gap filler 210 rests upon foot section 242 of mattress 14, the portion of rail-facing surface 226 near end wall 232 abuts inner surface 70 of foot end siderail 22, and wedge 236 abuts footboard 24. In this position bottom surface 230 is also positioned over any mattress gap 85 that may exist between inner surface 70 of foot end siderail 22 and mattress 14 as shown in FIG. 10. When retractable foot section 40 of bed 10 is fully extended, gap filler 210 extends between footboard 24 and foot end siderail 22 to close gaps 26, 28 therebetween as shown, for example, in FIGS. 10–12. As foot section 40 is retracted, bottom surface 230 of gap filler 210 slides along mattress 14 in the direction of arrow 246 in FIG. 11 more of rail-facing surface 226 near end wall 232 of gap filler 210 abuts siderail 22 as end wall 232 is pushed toward the head of bed 10. As foot section 40 of bed 10 is extended bottom surface 230 of gap filler 210 slides along mattress 14 in the direction of arrow 248 in FIG. 12 to return to the position shown in FIG. 10. Thus, gap filler 210 closes gaps 26, 28 between foot end siderails 22 and footboard 24 while retractable foot section 40 is in both the extended and retracted positions without inhibiting extension or retraction of foot section 40 of bed 10.

Although the invention has been described in detail with reference to preferred embodiments, variations and modifications exist within the scope and spirit of the invention as described and defined in the following claims.

What is claimed is:

1. A bed comprising
   a bedframe having a head end and a foot end,
   a mattress positioned on the bedframe,
   a siderail coupled to the bedframe, a board coupled to one of the head and foot ends of the bedframe, the siderail and the board cooperating to define a gap therebetween, and a gap filler coupled to the board to extend between the board and the siderail to substantially fill the gap defined therebetween.

2. The bed of claim 1, wherein the board includes a base coupled to the bedframe and a handle coupled to the base, the handle cooperates with the base to define a handle hole, the gap filler includes a barrier and a strap coupled to the barrier, and the strap extends through the handle hole to couple the barrier to the board.

3. The bed of claim 1, wherein the gap filler abuts the footboard and the siderail.

4. The bed of claim 1, wherein the bedframe includes a deck having a retractable foot section movable between a retracted position having a first length and an extended position having a second length greater than the first length, the gap filler moves relative to the siderail during movement of the retractable foot section between the retracted and extended positions.

5. The bed of claim 1, wherein the gap filler is rigid.

6. The bed of claim 1, wherein the gap filler includes a cover and a compressible filler.

7. The bed of claim 6, wherein the cover is formed from a water impermeable material and the compressible filler is formed from a foam material.

8. The bed of claim 1, wherein the gap filler includes a top surface and a bottom surface positioned to slide on the mattress.

9. A bed comprising a bedframe, a mattress positioned on the bedframe, a first barrier coupled to the bedframe, a second barrier coupled to the bedframe, the first and second barriers cooperating to define a gap therebetween, and a gap filler positioned to extend between the first and second barriers to substantially fill the gap defined therebetween, the gap filler including a top surface and a bottom surface positioned to slide on the mattress during movement of the gap filler relative to the mattress.

10. The bed of claim 9, wherein the bedframe includes a deck having a retractable foot section movable between a retracted position having a first length and an extended position having a second length greater than the first length, and the bottom surface of the gap filler slides on the mattress during movement of the retractable foot section between the retracted and extended positions.

11. The bed of claim 9, wherein the second baffler is a footboard coupled to the bedframe.

12. The bed of claim 11, the bed further comprising a footpad coupled to the footboard.

13. The bed of claim 9, wherein the first baffler is a footboard coupled to the bedframe and the second baffler is a siderail coupled to the bedframe.

14. The bed of claim 9, wherein the gap filler abuts the first baffler and slides along the first barrier.

15. A bed comprising a bedframe, a mattress positioned on the bedframe, a siderail coupled to the bedframe, the mattress and the siderail cooperating to define a mattress gap therebetween, a footboard coupled to the bedframe, the siderail and the footboard cooperating to define a substantial foot end gap therebetween, and a gap filler positioned on the mattress to substantially block the foot end gap and block at least a portion of the mattress gap.

16. The bed of claim 15, wherein the bedframe includes an articulating deck configured to support the mattress in a plurality of support configurations.

17. The bed of claim 15, wherein the gap filler includes a top surface and a bottom surface positioned to slide along the mattress during movement of the gap filler relative to the mattress.

18. The bed of claim 15, wherein the gap filler is coupled to the footboard.

19. The bed of claim 15, wherein the gap filler is rigid.

20. The bed of claim 15, wherein the gap filler is wider than the gap defined by the mattress and the siderail.

21. The bed of claim 15, wherein the siderail and the footboard cooperate to define a distance therebetween defining the foot end gap, the siderail includes a rail member having a height, and the distance between the siderail and the footboard is greater than the height of the rail member.

22. The bed of claim 15, wherein the gap filler extends completely from the footboard to the siderail.

23. The bed of claim 15, wherein the gap filler only blocks a portion of the mattress gap defined between the siderail and the mattress.

* * * * *